United States Patent
Nakai et al.

(10) Patent No.: US 10,182,775 B2
(45) Date of Patent: Jan. 22, 2019

(54) X-RAY COMPUTED TOMOGRAPHY APPARATUS INCLUDING A FIRST X-RAY DETECTOR AND A SECOND X-RAY DETECTOR FOR COUNTING X-RAY PHOTONS

(71) Applicant: Toshiba Medical Systems Corporation, Otawara-shi (JP)

(72) Inventors: Hiroaki Nakai, Nasushiobara (JP); Daizo Oikawa, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 587 days.

(21) Appl. No.: 14/873,710

(22) Filed: Oct. 2, 2015

(65) Prior Publication Data
US 2016/0022243 A1  Jan. 28, 2016

Related U.S. Application Data

(63) Continuation of application No. PCT/JP2014/059978, filed on Apr. 4, 2014.

(30) Foreign Application Priority Data

Apr. 4, 2013  (JP) ................................. 2013-078618

(51) Int. Cl.
*A61B 6/03* (2006.01)
*A61B 6/00* (2006.01)
(Continued)

(52) U.S. Cl.
CPC ............ *A61B 6/4241* (2013.01); *A61B 6/032* (2013.01); *A61B 6/0407* (2013.01); *A61B 6/06* (2013.01);
(Continued)

(58) Field of Classification Search
CPC ......... A61B 6/032; A61B 6/06; A61B 6/4035; A61B 6/4042; A61B 6/4085;
(Continued)

(56) References Cited

U.S. PATENT DOCUMENTS 4,995,107 A * 2/1991 Klingenbeck .......... A61B 6/032
378/19
5,684,855 A * 11/1997 Aradate .................. A61B 6/032
378/145
(Continued)

FOREIGN PATENT DOCUMENTS

JP  2006-101926 A  4/2006
JP  2006-346460 A  12/2006
(Continued)

OTHER PUBLICATIONS

International Search Report dated Jul. 15, 2014 in PCT/JP2014/059978 filed Apr. 4, 2014, with English translation.
(Continued)

*Primary Examiner* — Allen C. Ho
(74) *Attorney, Agent, or Firm* — Oblon, McClelland, Maier & Neustadt, L.L.P.

(57) ABSTRACT

An X-ray computed tomography apparatus according to an embodiment stores a plurality of reference count data indicative of energy spectra of X-rays, which are associated with a plurality of tube voltages or tube currents. Estimation circuitry estimates a tube voltage or a tube current at a time of X-ray irradiation, based on a comparison of energy spectra between second count data and each of the plurality of reference count data. Correction circuitry corrects first count data acquired together with the second count data, by using an energy spectrum calculated based on the estimated
(Continued)

tube voltage or tube current. Reconstruction circuitry reconstructs medical image data, based on the corrected first count data.

10 Claims, 6 Drawing Sheets

(51) Int. Cl.
  *A61B 6/06* (2006.01)
  *A61B 6/04* (2006.01)
(52) U.S. Cl.
  CPC .......... *A61B 6/4035* (2013.01); *A61B 6/4042* (2013.01); *A61B 6/4085* (2013.01); *A61B 6/4208* (2013.01); *A61B 6/4233* (2013.01); *A61B 6/461* (2013.01); *A61B 6/482* (2013.01); *A61B 6/483* (2013.01); *A61B 6/58* (2013.01)
(58) Field of Classification Search
  CPC ... A61B 6/4208; A61B 6/4233; A61B 6/4241; A61B 6/482; A61B 6/483
  USPC .................... 378/7, 19, 98.8, 98.9, 98.11, 5; 250/370.09
  See application file for complete search history.

(56) References Cited

U.S. PATENT DOCUMENTS

| | | | | |
|---|---|---|---|---|
| 6,470,067 B1* | 10/2002 | Harding | ............... | A61B 6/032 378/19 |
| 6,879,657 B2* | 4/2005 | Hoffman | ............... | A61B 6/032 378/19 |
| 6,925,140 B2* | 8/2005 | Bruder | ............... | A61B 6/4233 378/19 |
| 7,092,481 B2* | 8/2006 | Hoffman | ............... | A61B 6/4241 250/370.09 |
| 7,149,278 B2* | 12/2006 | Arenson | ............... | A61B 6/4241 378/19 |
| 7,260,174 B2* | 8/2007 | Hoffman | ............... | A61B 6/032 250/363.09 |
| 7,263,167 B2* | 8/2007 | Walter | ............... | A61B 6/032 378/116 |
| 7,453,974 B2* | 11/2008 | Van Steven-Daal | ............... | A61B 6/032 378/207 |
| 7,474,728 B2* | 1/2009 | Schlomka | ............... | A61B 6/032 378/6 |
| 7,480,362 B2* | 1/2009 | Carmi | ............... | A61B 6/032 378/19 |
| 7,502,437 B2* | 3/2009 | Schlomka | ............... | A61B 6/032 378/6 |
| 7,532,703 B2* | 5/2009 | Du | ............... | A61B 6/032 378/116 |
| 7,551,709 B2* | 6/2009 | Schlomka | ............... | A61B 6/032 378/57 |
| 7,587,021 B2* | 9/2009 | Schlomka | ............... | A61B 6/032 378/6 |
| 7,590,215 B2* | 9/2009 | Schlomka | ............... | A61B 6/032 378/4 |
| 7,613,274 B2* | 11/2009 | Tkaczyk | ............... | A61B 6/032 378/19 |
| 7,738,625 B2* | 6/2010 | Nishide | ............... | A61B 6/032 378/19 |
| 7,885,372 B2* | 2/2011 | Edic | ............... | A61B 6/032 378/158 |
| 7,968,853 B2* | 6/2011 | Altman | ............... | A61B 6/032 250/366 |
| 7,970,096 B2* | 6/2011 | Pavlovich | ............... | A61B 6/032 378/156 |
| 8,009,794 B2* | 8/2011 | Partain | ............... | A61B 6/032 378/150 |
| 8,077,826 B2* | 12/2011 | Ruimi | ............... | A61B 6/032 378/19 |
| 8,111,803 B2* | 2/2012 | Edic | ............... | A61B 6/4035 378/146 |
| 8,189,736 B2* | 5/2012 | Hirokawa | ............... | A61B 6/032 378/15 |
| 8,213,566 B2* | 7/2012 | Roessl | ............... | A61B 5/4869 378/5 |
| 8,299,440 B2* | 10/2012 | Wainer | ............... | G01T 1/17 250/363.04 |
| 8,338,791 B2* | 12/2012 | Proksa | ............... | G01T 1/171 250/369 |
| 8,373,135 B2* | 2/2013 | Kappler | ............... | G01T 1/247 250/336.1 |
| 8,378,307 B2* | 2/2013 | Baeumer | ............... | G01T 1/2985 250/362 |
| 8,384,038 B2* | 2/2013 | Guo | ............... | G01T 1/247 250/370.09 |
| 8,442,184 B2* | 5/2013 | Forthmann | ............... | A61B 6/032 378/5 |
| 8,483,352 B2* | 7/2013 | Hoffman | ............... | A61B 6/032 378/19 |
| 8,483,353 B2* | 7/2013 | Hoffman | ............... | A61B 6/032 378/19 |
| 8,488,854 B2* | 7/2013 | Arenson | ............... | G06T 11/005 378/1 |
| 8,611,489 B2* | 12/2013 | Roessl | ............... | G01T 1/1647 378/5 |
| 8,619,943 B2* | 12/2013 | Flohr | ............... | A61B 6/032 378/19 |
| 8,774,350 B2* | 7/2014 | Tsubota | ............... | A61B 6/032 378/19 |
| 8,873,703 B2* | 10/2014 | Ruimi | ............... | A61B 6/032 250/370.09 |
| 8,891,845 B2* | 11/2014 | Ogawa | ............... | A61B 6/14 382/128 |
| 8,913,711 B2* | 12/2014 | Moriyasu | ............... | A61B 6/03 378/4 |
| 8,941,076 B2* | 1/2015 | Abraham | ............... | G01T 1/171 250/336.1 |
| 9,000,385 B2* | 4/2015 | Dror | ............... | G01T 1/171 250/370.06 |
| 9,014,330 B2* | 4/2015 | Takayama | ............... | A61B 6/032 250/363.02 |
| 9,044,189 B2* | 6/2015 | Flohr | ............... | A61B 6/032 |
| 9,052,266 B2* | 6/2015 | Miyazaki | ............... | A61B 6/4241 |
| 9,164,183 B2* | 10/2015 | Kraft | ............... | G01T 1/40 |
| 9,176,238 B2* | 11/2015 | Herrmann | ............... | G01T 1/17 |
| 9,208,585 B2* | 12/2015 | Leng | ............... | A61B 6/032 |
| 9,216,302 B2* | 12/2015 | Kuwahara | ............... | A61N 5/1039 |
| 9,268,035 B2* | 2/2016 | Herrmann | ............... | G01T 1/17 |
| 9,274,235 B2* | 3/2016 | Kang | ............... | G01N 23/04 |
| 9,301,378 B2* | 3/2016 | Steadman Booker | .... | G01T 1/24 |
| 9,316,745 B2* | 4/2016 | Noshi | ............... | G01T 1/17 |
| 9,335,424 B2* | 5/2016 | Herrmann | ............... | G01T 1/171 |
| 9,351,701 B2* | 5/2016 | Yamakawa | ............... | A61B 6/025 |
| 9,354,331 B2* | 5/2016 | Sagoh | ............... | A61B 6/032 |
| 9,389,320 B2* | 7/2016 | Ogawa | ............... | A61B 6/14 |
| 9,417,339 B2* | 8/2016 | Spahn | ............... | G01T 1/247 |
| 9,480,444 B2* | 11/2016 | Kappler | ............... | A61B 6/032 |
| 9,532,759 B2* | 1/2017 | Taguchi | ............... | A61B 6/032 |
| 9,535,167 B2* | 1/2017 | Proksa | ............... | G01T 1/171 |
| 9,572,540 B2* | 2/2017 | Zhang | ............... | H01L 27/14634 |
| 9,579,075 B2* | 2/2017 | Besson | ............... | G01T 1/2985 |
| 9,595,101 B2* | 3/2017 | Kato | ............... | G06T 11/005 |
| 9,619,730 B2* | 4/2017 | Pavlovich | ............... | A61B 6/032 |
| 9,633,814 B2* | 4/2017 | Oikawa | ............... | A61B 6/405 |
| 9,746,566 B2* | 8/2017 | Herrmann | ............... | G01T 1/247 |
| 9,747,704 B2* | 8/2017 | Taguchi | ............... | G06T 11/005 |
| 9,795,353 B2* | 10/2017 | Teshigawara | ........ | A61B 6/5205 |
| 9,808,210 B2* | 11/2017 | Yamazaki | ............... | A61B 6/032 |
| 9,924,916 B2* | 3/2018 | Kato | ............... | A61B 6/4208 |

(56) References Cited

U.S. PATENT DOCUMENTS

2006/0280281 A1 12/2006 Flohr et al.
2008/0260094 A1 10/2008 Carmi
2009/0220043 A1 9/2009 Nishide et al.

FOREIGN PATENT DOCUMENTS

| JP | 2009-513220 A | 4/2009 |
| JP | 2009-201885 A | 9/2009 |
| JP | 2010-082031 A | 4/2010 |
| JP | 2011-217805 A | 11/2011 |

OTHER PUBLICATIONS

Written Opinion dated Jul. 15, 2014 in PCT/JP2014/059978 filed Apr. 4, 2014.

* cited by examiner

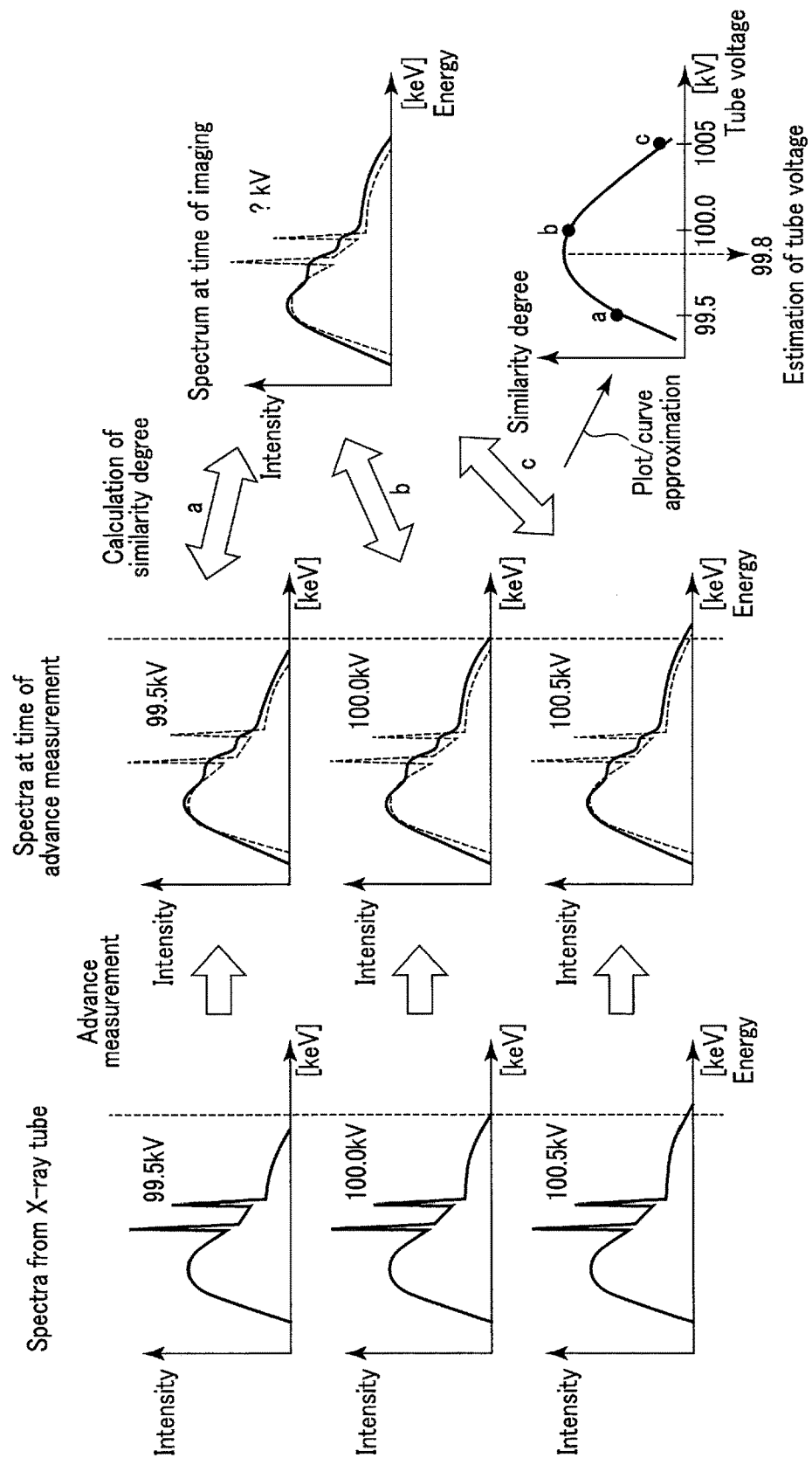
F I G. 3

X-RAY COMPUTED TOMOGRAPHY APPARATUS INCLUDING A FIRST X-RAY DETECTOR AND A SECOND X-RAY DETECTOR FOR COUNTING X-RAY PHOTONS

CROSS-REFERENCE TO RELATED APPLICATIONS

This application is a Continuation application of PCT application No. PCT/JP2014/059978, filed on Apr. 4, 2014, and is based upon and claims the benefit of priority from Japanese Patent Application No. 2013-078618, filed on Apr. 4, 2013, the entire contents of which are incorporated herein by reference.

FIELD

Embodiments described herein relate generally to an X-ray computed tomography apparatus.

BACKGROUND

Conventionally, in X-ray computed tomography apparatuses (hereinafter, also referred to as X-ray CT apparatuses), there is a case in which the dosage of X-rays (hereinafter, also referred to as "X-ray dosage"), which are radiated from an X-ray tube, varies at each time due to a factor such as a ripple of an X-ray tube voltage or a change with time. In this case, the dosage of the X-rays that pass through a subject and are detected by an X-ray detector also varies, resulting in a problem that a tomogram cannot exactly be reconstructed.

In the X-ray CT apparatus, in order to prevent this problem, a correction detector (reference detector) is disposed at a position where X-rays pass through only a region of air, or only a wedge filter, without passing through the subject, and the output of the X-ray detector is corrected based on the output of the correction detector. Since the output of the conventional X-ray detector is an integration-type output, it should suffice if the correction detector observes the total amount (the detector output relative to the total amount) in the entire energy range of X-rays. The integration-type output means an output indicative of a result of integration in the entire energy band of a product between an X-ray energy value and a detector sensitivity at this energy value.

On the other hand, there is known a photon-counting-type X-ray CT apparatus as an X-ray CT apparatus of a type different from the integration type. In the photon-counting-type X-ray CT apparatus, the main object is to acquire a tomogram at each X-ray energy or at each X-ray energy band (energy bin).

In this type of X-ray CT apparatus, there is known a method in which energy information of X-rays is specified by using a second X-ray detector of a photon-counting type. In this method, for example, when imaging is performed by switching an X-ray tube voltage on a view-by-view basis, such as when dual-energy imaging is performed, the energy information of X-rays, which are radiated from the X-ray tube, can be specified by the second X-ray detector. However, the energy information of X-rays, in this context, is information by which the X-ray dosage of a view can be acquired by using, e.g., an average value of a specific energy range, but this information is not information by which the energy spectrum of X-rays, which are radiated from the X-ray tube, can be estimated or corrected.

However, in the photon-counting-type X-ray CT apparatus, when the X-ray energy spectrum varies, although the X-ray dosage (the total or average value of the energy in the entire or specific range) can be observed by using a photon-counting-type X-ray detector, the variation of the X-ray dosage at each energy or at each energy band cannot be corrected. Thus, in the photon-counting-type X-ray CT apparatus, there is a problem that a tomogram at each energy or at each X-ray energy band cannot be reconstructed.

As described above, in the photon-counting-type X-ray CT apparatus, there is the problem that, when the energy spectrum of X-rays radiated from the X-ray tube varies, a tomogram at each energy or at each X-ray energy band cannot be reconstructed.

It is an object to provide an X-ray computed tomography apparatus which can correct a variation of the energy spectrum of X-rays radiated from an X-ray tube, and can exactly reconstruct a tomogram at each energy or at each energy band.

BRIEF DESCRIPTION OF THE DRAWINGS

FIG. 3 is a diagram for explaining a correction method of an X-ray energy spectrum in the embodiment.

DETAILED DESCRIPTION

In general, according to one embodiment, an X-ray computed tomography apparatus includes an X-ray tube, a first X-ray detector, a second X-ray detector, count result acquisition circuitry, memory circuitry, estimation circuitry, correction circuitry, and reconstruction circuitry.

The X-ray tube is configured to radiate X-rays.

The first X-ray detector is configured to count X-ray photons in a first region of the radiated X-rays, and to acquire energy of the X-ray photons.

The second X-ray detector is configured to count X-ray photons in a second region of the radiated X-rays, and to acquire energy of the X-ray photons.

The count result acquisition circuitry acquires count results of the first and second X-ray detectors, and outputs first and second count data indicative of energy spectra of X-rays.

The memory circuitry stores a plurality of reference count data indicative of energy spectra of X-rays, which are associated with a plurality of tube voltages or tube currents for radiating X-rays from the X-ray tube.

The estimation circuitry estimates a tube voltage or a tube current at a time of X-ray irradiation, based on a comparison of energy spectra between the second count data and each of the plurality of reference count data.

The correction circuitry corrects the first count data acquired together with the second count data, by using an energy spectrum calculated based on the estimated tube voltage or tube current.

The reconstruction circuitry is configured to reconstruct medical image data, based on the corrected first count data.

Computed tomography apparatuses (X-ray CT apparatuses) according to various embodiments will be described hereinafter with reference to the accompanying drawings.

First Embodiment

Figure 1:
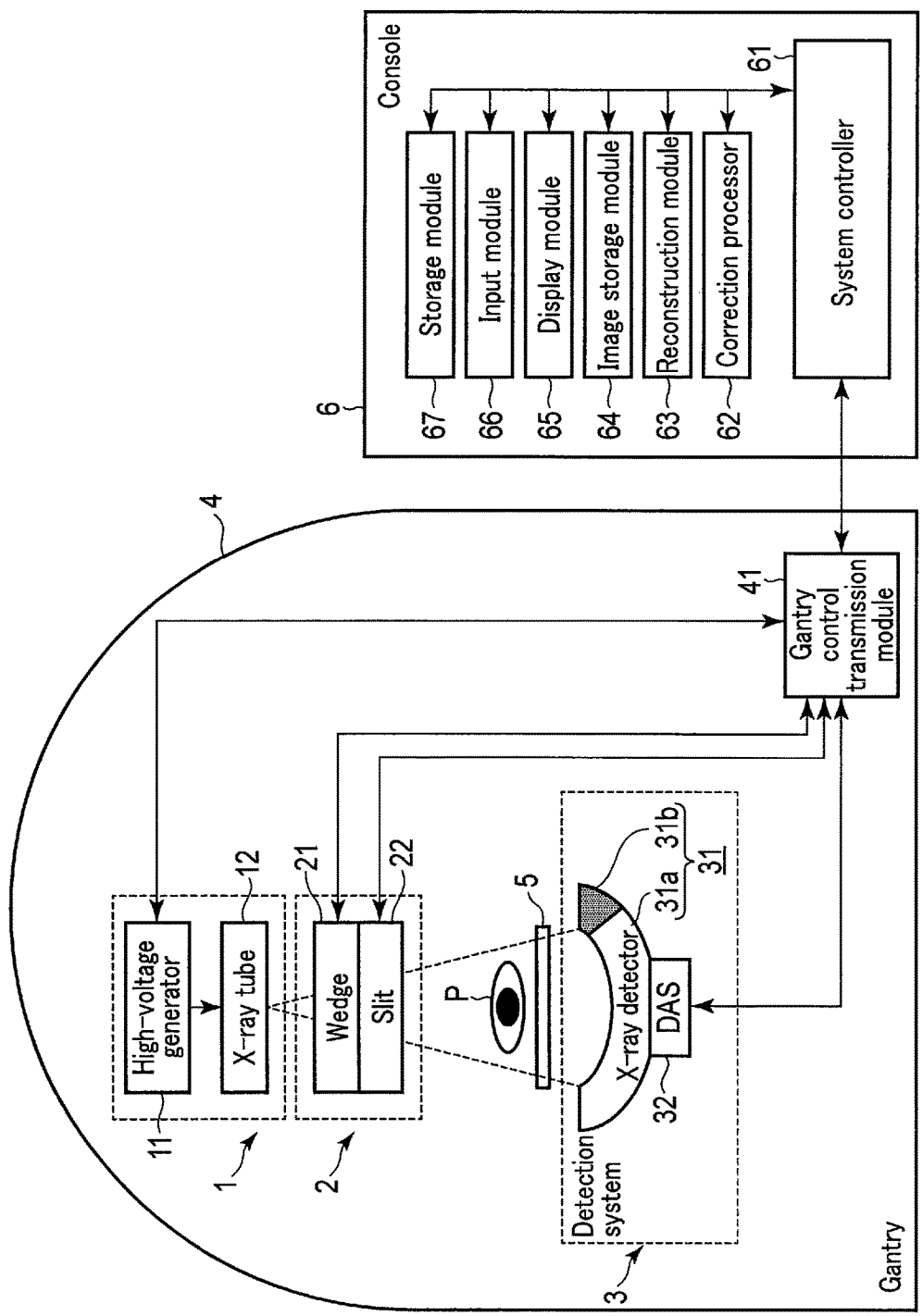
FIG. 1 is a diagram illustrating a configuration of an X-ray CT apparatus according to a first embodiment.
Figure 2:
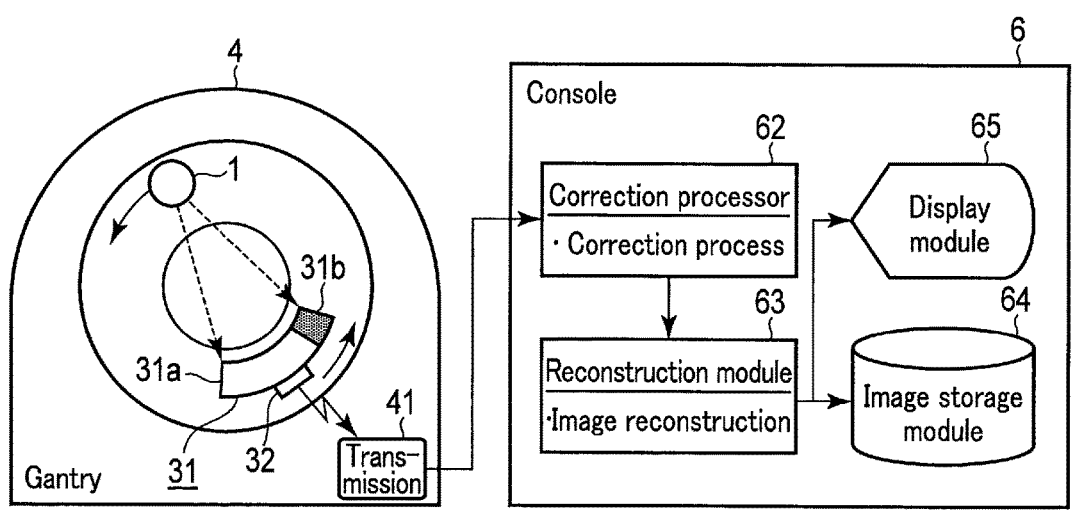
FIG. 2 is a diagram illustrating a schematic configuration of the X-ray CT apparatus in the embodiment.

FIG. 1 is a block diagram illustrating a configuration of an X-ray CT apparatus according to a first embodiment. FIG. 2 is a diagram illustrating a schematic configuration of the X-ray CT apparatus. In this X-ray CT apparatus, as illustrated in FIG. 1, a gantry 4 and a console 6 are electrically connected. In addition, the X-ray CT apparatus includes a table 5 on which a subject P is placed. In the gantry 4, a pair of systems, consisting of an X-ray system 1 and an optical system 2, on one hand, and a detection system 3, on the other hand, are accommodated, and a rotational support mechanism (not shown), which rotates this pair of systems 1 and 3 about a body axis of the subject P on the table 5, is accommodated. The rotational support mechanism includes a rotary ring, a ring support mechanism which supports the rotary ring so as to be rotatable about a rotational axis Z, and a driving module for driving the rotation of the ring. An X-ray tube 12 and an X-ray detector 31 of a so-called two-dimensional array type or a multi-column type are mounted on the rotary ring. At a time of imaging or scanning, the subject P is placed on the table 5 and inserted in a cylindrical imaging region between the X-ray tube 12 and the X-ray detector 31 in the gantry 4.

The X-ray system 1, optical system 2 and detection system 3 are controlled by a gantry control transmission module 41 in the gantry 4. The gantry control transmission module 41 is transmissibly connected to a system controller 61 in the console 6. The console 6 includes the system controller 61, a correction processor 62, a reconstruction module 63, an image storage module 64, a display module 65, an input module 66, and a storage module 67.

Here, the X-ray system 1 includes a high-voltage generator 11 and X-ray tube 12.

The high-voltage generator 11 includes a high-voltage power supply (not shown) for applying a high voltage between an anode target and a cathode filament of the X-ray tube 12, and a filament current generator (not shown) for supplying a filament current to the cathode filament of the X-ray tube 12.

The X-ray tube 12 generates X-rays by receiving the application of the voltage (hereinafter referred to as "tube voltage") and the supply of the filament current from the high-voltage generator 11 via a slip ring (not shown), and radiates (irradiates) the X-rays from the focal point of X-rays. The X-rays radiated from the focal point of X-rays are shaped, for example, in a cone beam shape (pyramidal shape), via a wedge 21 and a slit 22 in the optical system 2 attached to an X-ray radiation window of the X-ray tube 12. Incidentally, the wedge 21 is a filter for reducing radiation exposure, and the slit 22 is a gap for beam shaping. The radiation range of X-rays is indicated by a broken line. An X axis is a straight line which is perpendicular to the rotational axis Z and passes through the focal point of radiated X-rays. A Y axis is a straight line which is perpendicular to the X axis and the rotational axis Z. It is assumed that the X-ray tube 12 in the present embodiment is an X-ray tube of a rotary anode type. Incidentally, X-ray tubes of other types, excluding an X-ray tube of a fixed anode type, are also applicable to the present embodiment.

On the other hand, the detection system 3 includes the X-ray detector 31 and a data-acquisition module (DAS) 32.

The X-ray detector 31 is attached at such a position and an angle as to be opposed to the X-ray tube 12, with the rotational axis Z interposed. The X-ray detector 31 includes a plurality of X-ray detection elements which are arrayed in a grid shape in a channel direction which is perpendicular to the body axis of the subject P (or the direction of the rotational axis Z), and in a column direction along the body axis of the subject P. In the meantime, an X-ray detector, which is located in a second region (e.g., one end region in the channel direction) of the X-ray detector 31, is also referred to as a second X-ray detector 31b, and an X-ray detector, which is located in a first region (e.g., the region other than the second X-ray detector 31b), is referred to as a first X-ray detector 31a. The first region may be set as a region including at least a region corresponding to the subject P placed on the table 5. The second region is a region different from the first region. In this example, the second X-ray detector 31b is provided to be continuous with an end portion of the first X-ray detector 31a. The channel direction may be a direction of an arc which is perpendicular to the rotational axis Z, has a center at a focal point of radiated X-rays, and has a radius corresponding to a distance from this center to a middle point of light-reception parts of X-ray detection elements corresponding to one channel. The column direction may also be called a slice direction. The second X-ray detector 31b may be called a correction detector or a reference detector.

Although, by way of example, the case has been illustrated in which the second X-ray detector 31b is provided to be continuous with an end portion of the first X-ray detector 31a, the position of the second X-ray detector 31b is not limited to this. Since it should suffice if the second X-ray detector 31b is provided at a position where X-rays do not pass the subject P, the second X-ray detector 31b does not necessarily need to be continuous with the detector 31a, and the second X-ray detector 31b may be disposed spaced apart from the first X-ray detector 31a, disposed near the X-ray tube 12 or wedge 21, or disposed fixedly at an arbitrary position within the rotary section. In addition, the second X-ray detector 31b may be provided at a position where X-rays do not pass the wedge 21 and the subject P. In addition, the second X-ray detector 31b may be provided at a position where X-rays directly enter the second X-ray detector 31b without passing through the wedge 21 nor the subject P.

The first and second X-ray detectors 31a and 31b have the same configuration. However, the first X-ray detector 31a counts X-ray photons in the first region of radiated X-rays, and acquires energy of the X-ray photons. The second X-ray detector 31b counts X-ray photons in the second region of radiated X-rays, and acquires energy of the X-ray photons. For example, the first X-ray detector 31a counts X-ray photons which were radiated from the X-ray tube 12 and passed through the subject P, and acquires the energy of the X-ray photons. The second X-ray detector 31b counts X-ray photons which were radiated at the same time as the radiation to the subject P, but did not pass through the subject P, and acquires the energy of the X-ray photons. In addition, since it should suffice if the second X-ray detector 31b is disposed at the position where X-rays radiated from the X-ray tube 12 pass through only the region of air or only the wedge 21, the second X-ray detector 31b may be disposed, for example, in an end region between the X-ray tube 12 and wedge 21 or the outside of wedge 21. The end region between the X-ray tube 12 and wedge 21 or the outside of wedge 21 may also be called a vicinity of the X-ray tube 12.

In any case, a collimator, which narrows the directivity of incident X-rays, is attached to each of the plural X-ray detection elements in the X-ray detector 31a, 31b. Each of the plural X-ray detection elements in the X-ray detector 31a converts the X-rays, which were radiated from the X-ray tube 12 and passed through the subject P, to photons, and detects the photons. Similarly, each of the plural X-ray detection elements in the X-ray detector 31b converts the X-rays, which were radiated from the X-ray tube 12 but did not pass through the subject P, to photons, and detects the photons. For example, X-rays, which have passed through the subject P, are incident on the X-ray detection element. The X-rays incident on the X-ray detection element are narrowed by the collimator, made incident on a scintillator, and converted to photons. The photons enter a photodiode and generate an electric charge, and the stored charge is released by a bias voltage applied to the photodiode. The released charge is stored through a read-out line by a CMOS switch functioning as a read-out switch, and a first detection signal having a wave height corresponding to the energy of X-rays is generated. First detection signals from the plural X-ray detection elements are output (read out) to a counter (not shown) via a connection switch module (not shown). The counter counts the number of first detection signals with respect to each predetermined wave height range, and outputs a count result to the data-acquisition module (DAS) 32. In the meantime, when X-rays, which were radiated at the same time as the radiation to the subject P but did not pass through the subject P, were incident on the X-ray detection element, a second detection signal having a wave height corresponding to the energy of X-rays is similarly generated and output. Likewise, the counter counts the number of second detection signals with respect to each predetermined wave height range, and outputs a count result to the data-acquisition module (DAS) 32. Incidentally, as the X-ray detector 31, use may be made of a direct-conversion-type semiconductor detector which does not use a scintillator. Additionally, the operation of converting X-rays to photons and detecting the photons may be an operation of detecting X-ray photons. Additionally, it should suffice if the X-ray detector 31 can count X-ray photons, and use may be made of an arbitrary detector such as a detector using a SiPM (silicon photomultiplier), or a detector using CdTe or germanium. Additionally, although the set number of the predetermined wave height range is arbitrary, the number of detection signals is counted with respect to each energy band when the set number is small, and the number of detection signals is counted with respect to each energy when the number set number is large. In short, the fineness of discrimination of wave height ranges corresponds to the fineness of energy band resolution.

The data-acquisition module (DAS) 32 includes a plurality of data-acquisition circuits which constitute count result acquisition circuitry. The count result acquisition circuitry acquires count results of the first and second X-ray detectors 31a, 31b, and outputs first and second count data indicative of X-ray energy spectra. Specifically, for example, the plural data-acquisition circuits acquire a count result of first detection signals which are individually read out from the respective X-ray detection elements, and output to the gantry control transmission module 41 first count data (which is composed of the acquired count result) indicating an energy spectrum of X-rays which have passed through the subject P. Similarly, the plural data-acquisition circuits acquire a count result of second detection signals which are individually read out from the respective X-ray detection elements, and outputs to the gantry control transmission module 41 second count data (which is composed of the acquired count result) indicating an energy spectrum of X-rays which did not pass through the subject P. In general, the number of data-acquisition circuits is less than the number of X-ray detection elements. The data-acquisition circuits, the number of which is equal to the number of output terminals (or switches) of connection switch modules (not shown), are provided, and each data-acquisition circuit is implemented, for example, for each channel (ch) of each segment.

The gantry control transmission module 41 sends the first count data and second count data, which were received from the data-acquisition module (DAS) 32, to the correction processor 62 via the system controller 61.

The correction processor 62 constitutes estimation circuitry for estimating a tube voltage or a tube current at a time of X-ray irradiation, based on a comparison of energy spectra of the second count data and plural reference data. In addition, the correction processor 62 constitutes correction circuitry for correcting the first count data obtained together with the second count data, by using an energy spectrum calculated based on the estimated tube voltage or tube current.

Specifically, for example, if the correction processor 62 receives the first count data and second count data from the data-acquisition module 32 via the gantry control transmission module 41 and system controller 61, the correction processor 62 corrects the first count data, based on the second count data. In the correction based on the second count data, for example, a variation of the tube voltage of the X-ray tube 12 is detected by the second X-ray detector 31b, and the energy spectrum is estimated based on the second count data that is obtained by collecting the acquired second detection signals. Thereafter, a reference process is executed which normalizes the first count data at each energy band, based on third count data indicative of the estimated energy spectrum, and corrects a variation in X-ray intensity.

Specifically, the correction based on the second count data can be executed by the following functions (f62-1) to (f62-3).

(f62-1) A first estimation function of comparing the second count data and each of a plurality of reference count data, and estimating a tube voltage or a tube current, which corresponds to reference count data having a highest similarity degree, as a tube voltage or a tube current at a time of X-ray irradiation. Specifically, a first estimation function, as illustrated in an example of FIG. 3, of calculating similarity degrees between the respective reference count data in the storage module 67 and the second count data, and estimating a tube voltage (or a tube current) of the X-ray tube 12 at a time of irradiation to the subject P, based on the calculated similarity degrees and each reference count data. Incidentally, the respective graphs in the middle column in FIG. 3 correspond to the respective reference count data in the storage module 67. A graph shown in the upper part of the right column in FIG. 3 corresponds to the second count data. A graph shown in the lower part of the right column in FIG. 3 corresponds to an estimation process.

Here, in the first estimation function (f62-1), a tube voltage (100.0 kV corresponding to point b in the lower right part of FIG. 3) of the reference count data having a highest similarity degree (b in FIG. 3) among the calculated similarity degrees may be estimated as the tube voltage (or tube current) at the time of irradiation to the subject P. In addition, instead of the first estimation function (f62-1), similarity degrees between the second count data and the plural reference count data may be calculated, and, furthermore, the respective similarity degrees may be approximated by a curve, and a tube voltage or a tube current relating to a similarity degree at a time when the curve takes the maximum value may be estimated as the tube voltage or tube current at the time of X-ray irradiation. For example, the relationship between the calculated similarity degrees and the tube voltages (or tube currents) of the respective reference count data having these similarity degrees may be approximated by a curve, and a tube voltage (99.8 kV indicated by a broken line in the lower right part of FIG. 3) (or tube current), which relates to the similarity at a time when the curve takes the maximum value, may be estimated as the tube voltage (or tube current) at the time of irradiation to the subject P.

(f62-2) A second estimation function of estimating, based on an estimated tube voltage (or tube current) and each piece of reference count data, an energy spectrum of X-rays which were radiated with the estimated voltage (or tube current).

In the meantime, in the second estimation function (f62-2), based on the estimated tube voltage (or tube current) and two pieces of reference count data corresponding individually to two tube voltages (or tube currents) between which the estimated tube voltage (or tube current) lies, two energy spectra indicated by these reference count data may be interpolated (e.g., linear interpolation). Thereby, the energy spectrum of radiated X-rays may be estimated.

(f62-3) A correction function of correcting first count data, based on the estimated energy spectrum.

Here, the first and second estimation functions (f62-1) and (f62-2) are examples of the estimation circuitry. The correction function (f62-3) is an example of the correction circuitry.

The reconstruction module 63 reconstructs medical image data of the subject P, based on first count data which was corrected by the correction processor 62. For example, the reconstruction module 63 generates projection data, based on the corrected first count data. Specifically, the reconstruction module 63 generates the projection data by mutually adding a plurality of count results in the corrected first count data.

The projection data is data immediately before the reconstruction process, and is a set of data values corresponding to the intensity of X-rays which have passed through the subject P. The projection data is associated with data representative of a view angle at a time when data was acquired, and is stored in a storage module (not shown) including a magnetic disk, a magnetic optical disk or a semiconductor memory. Here, for the sake of convenience in description, a set of projection data over all channels with an identical view angle, at which data was acquired by one shot substantially at the same time, is referred to as a "projection data set". Incidentally, the projection data for each channel in the projection data set is identified by a view angle, a cone angle, and a channel number. The view angle represents an angle of each of positions on a circular orbit around which the X-ray tube 12 revolves about the rotational axis Z, within the range of 360° with the uppermost part of the circular orbit in the vertically upward direction from the rotational axis Z being set at 0°.

In addition, the reconstruction module 63 reconstructs medical image data representing a tomogram of the subject P, based on a projection data set in the range in which the view angle is 360° or 180°+a fan angle. Here, as regards the reconstruction method, for example, the method of Jpn. Pat. Appln. KOKAI Publication No. 2006-101926 can be applied to a desired energy band.

The image storage module 64 stores the medical image data which was reconstructed by the reconstruction module 63.

The display module 65 displays, for example, medical image data stored in the image storage module 64, and conditions which are set for X-ray computed tomography.

The input module 66 inputs, for example, imaging conditions for X-ray computed tomography desired by an operator, and information about the subject. Specifically, the input module 66 takes various instructions, commands, information, selection and settings from the operator into the X-ray CT apparatus. Although not illustrated, the input module 66 includes a track ball, a switch button, a mouse, a keyboard, etc. for setting a region-of-interest, etc. The input module 66 detects coordinates of a cursor which is displayed on the display screen, and outputs the detected coordinates to the system controller 61. Incidentally, the input module 66 may be a touch panel which is so provided as to cover the display screen. In this case, the input module 66 detects touch-instructed coordinates by a coordinate read principle of an electromagnetic induction method, an electromagnetic strain method, a pressure-sensing method, etc., and outputs the detected coordinates to the system controller 61.

The storage module (memory circuitry) 67 stores a plurality of reference count data indicative of X-ray energy spectra, which are associated with a plurality of tube voltages or tube currents for radiating X-rays from the X-ray tube 12. For example, the storage module 67 stores a plurality of reference count data indicative of X-ray energy spectra, which were obtained from the second X-ray detector 31b and data-acquisition module (DAS) 32 by radiating X-rays from the X-ray tube 12 with a plurality of preset tube voltages (or tube currents).

The system controller 61 functions as a central unit of the X-ray CT apparatus. The system controller 61 includes a CPU and a memory (not shown). The system controller 61 controls the table 5, gantry 4 and high-voltage generator 11 for X-ray computed tomography, based on inspection schedule data and a control program stored in a storage module (not shown). Specifically, the system controller 61 temporarily stores in a memory (not shown) information such as operator's instructions and conditions of image processing, which are sent from the input module 66. Based on the information temporarily stored in the memory, the system controller 61 controls the table 5 and gantry 4, and the high-voltage generator 11. The system controller 61 reads out from the memory module (not shown) a control program for executing predetermined image generation/display, develops the control program on its own memory, and executes arithmetic operations/processes, etc. relating to various processes.

Figure 4:
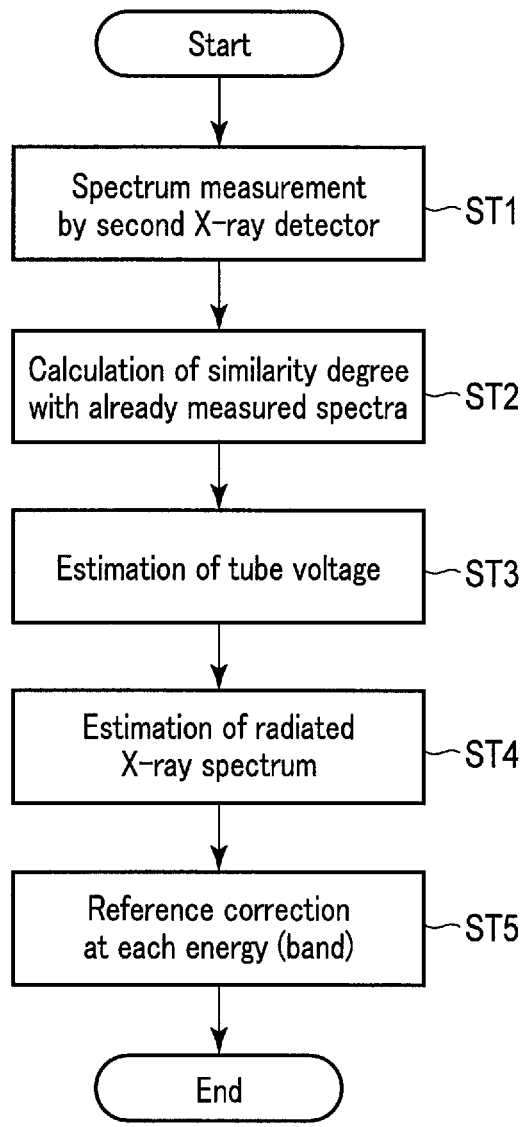
FIG. 4 is a flowchart for explaining an operation in the embodiment.

Next, the operation of the X-ray CT apparatus with the above-described configuration is described with reference to a flowchart of FIG. 4. In addition, the description of steps ST3 and ST4 is given by taking a tube voltage as an example, from between a tube voltage and a tube current. In other words, in the description of steps ST3 and ST4, "tube voltage" may be read as "tube current".

To start with, in the X-ray CT apparatus, X-rays are radiated from the X-ray tube 12 with a plurality of preset tube voltages, without using the subject P. At this time, a plurality of reference count data indicative of energy spectra of X-rays at the respective tube voltages are obtained by the second X-ray detector 31b and data-acquisition module (DAS) 32. The plural reference count data are stored in the storage module 67 via the gantry control transmission module 41 and system controller 61 (ST1). Thereby, the storage module 67 stores the plural reference count data indicative of X-ray energy spectra, which are associated with the plural tube voltages (or tube currents) for radiating X-rays from the X-ray tube 12.

A supplementary description is given of step ST1. If the tube voltage of the X-ray tube 12 varies, the energy spectrum of X-rays, which are radiated from the X-ray tube 12, that is, the distribution of X-ray intensity at each energy, varies as illustrated in the left part of FIG. 3.

Thus, before stating imaging of the subject P, the tube voltage is varied in advance in a predetermined range (e.g., 99.5 kV~100.5 kV), and X-ray energy spectra measured by the second X-ray detector are obtained (the middle column in FIG. 3). With the second X-ray detector 31b, due to the energy resolution of the detector, X-ray energy spectra (the left part in FIG. 3) radiated from the X-ray tube 12 cannot precisely be measured, and obtuse energy spectra are measured as indicated by solid lines in the middle part of FIG. 3. This measurement result is stored in the storage module 67 in advance.

Next, in the X-ray CT apparatus, imaging of the subject P is performed. Specifically, in the X-ray CT apparatus, the subject P is placed on the table 5 and inserted in the cylindrical imaging region between the X-ray tube 12 and X-ray detector 31, which rotate about the rotational axis Z. In this state, the X-ray tube 12 radiates X-rays. The first X-ray detector 31a counts X-ray photons in the first region of the radiated X-rays, and acquires the energy of the X-ray photons. For example, the first X-ray detector 31a converts the X-rays, which were radiated and passed through the subject P, to photons, and counts the number of first detection signals having a wave height corresponding to the energy of X-rays with respect to each predetermined wave height range.

The data-acquisition module (DAS) 32 acquires count results of the first X-ray detector 31a, and outputs first count data indicating an energy spectrum of X-rays which have passed through the subject P.

On the other hand, the second X-ray detector 31b counts X-ray photons in the second region of the radiated X-rays, and acquires the energy of the X-ray photons. For example, the second X-ray detector 31b converts the X-rays, which were radiated at the same time as the irradiation to the subject P but did not pass through the subject P, to photons, and counts the number of second detection signals having a wave height corresponding to the energy of X-rays with respect to each predetermined wave height range.

Similarly, the data-acquisition module (DAS) 32 acquires count results of the second X-ray detector 31b, and outputs second count data indicating an energy spectrum of X-rays which did not pass through the subject P.

Specifically, the data-acquisition module (DAS) 32 acquires the count results of the first and second X-ray detectors 31a and 31b, and outputs the first and second count data indicative of X-ray energy spectra.

The first and second count data are sent to the correction processor 62 via the gantry control transmission module 41 and system controller 61.

The correction processor 62 estimates the tube voltage or tube current at the time of X-ray irradiation, based on the comparison of energy spectra between the second count data and each of the plural reference count data (ST2~ST3).

For example, the correction processor 62 calculates the similarity degree between each reference count data in the storage module 67 and the second count data (ST2). As the similarity degree, use may be made of an arbitrary statistical amount representing a distance between multidimensional data, such as normalized correlation values.

Next, based on the calculated similarity degrees and the tube voltages of the respective reference count data, the correction processor 62 estimates the tube voltage of the X-ray tube 12 at the time of irradiation to the subject P (ST3). Here, in the estimation of the tube voltage, the tube voltage of the reference count data having the highest similarity degree may be estimated as the tube voltage. Specifically, the correction processor 62 may estimate, as the tube voltage at the time of irradiation to the subject P, a tube voltage (100.0 kV corresponding to point b in the lower right part of FIG. 3) of the reference count data having the highest similarity degree (b in FIG. 3) among the calculated similarity degrees. Alternatively, in the estimation of the tube voltage, the calculated similarity degrees may be interpolated. Specifically, the correction processor 62 may approximate, by a curve, the relationship between the calculated similarity degrees and the tube voltages of the reference count data having these similarity degrees, and may estimate a tube voltage (99.8 kV indicated by a broken line in the lower right part of FIG. 3), which relates to the similarity degree at a time when the curve takes the maximum value, as the tube voltage (or tube current) at the time of irradiation to the subject P. When the calculated similarity degrees were interpolated by curve approximation, the tube voltage can be estimated more precisely than in the case of the estimation from the highest similarity degree.

Next, the correction processor 62 corrects the first count data obtained together with the second count data, by using the energy spectrum calculated based on the estimated tube voltage (or tube current) (ST4~ST5).

For example, the correction processor 62 estimates the energy spectrum of X-rays radiated with the estimated tube voltage, based on the tube voltage estimated in step ST3 and each reference count data in the storage module 67 (ST4). The estimation of the energy spectrum may be executed by interpolation (e.g., linear interpolation) of the spectra of voltages in the neighborhood. Specifically, based on the estimated tube voltage and two reference count data corresponding individually to two tube voltages between which the estimated tube voltage lies, the correction processor 62 may linear-interpolate the two energy spectra indicated by these reference count data, and may estimate the energy spectrum of X-rays radiated with the estimated tube voltage.

The correction processor 62 corrects the first count data, based on the energy spectrum estimated in step ST4 (ST5).

Specifically, for example, the correction processor 62 may execute step ST5 by using reference correction which normalizes the first count data with respect to each energy (band), by dividing the first count data by third count data indicative of the estimated energy spectrum. Specifically, the correction processor 62 may execute step ST5 by using the method disclosed in Jpn. Pat. Appln. KOKAI Publication No. 2006-101926. In this case, the energy fluence of X-rays is $\Psi(E)'$, the energy spectrum of X-rays is $\varphi(E)$, and the energy weight function is $w(E)$, and it is assumed that the relational expression of these is set to be $\Psi(E)'=\varphi(E) \cdot w(E)$. Incidentally, the energy fluence $\Psi(E)'$ corresponds to the count result in each wave height range in the first count data after correction. The energy spectrum $\varphi(E)$ corresponds to the count result in each wave height range in the first count data before correction. The energy weight function $w(E)$ corresponds to a weighting factor for each energy (band) E in the energy spectrum estimated in step ST4. As the weighting factor, use is made of an inverse number of the X-ray intensity (=the count result in each wave height range of the second detection signal) at each energy (band) E in the energy spectrum φ(E)' estimated in step ST4.

The reconstruction module 63, in any case, reconstructs the medical image data of the subject P, based on the first count data corrected in step ST5. The reconstructed medical image data is written in the image storage module 64. The medical image data in the image storage module 64 is displayed by the display module 65.

As has been described above, according to the present embodiment, the plural reference count data indicative of X-ray energy spectra, which are associated with the plural tube voltages (or tube currents) for radiating X-rays from the X-ray tube 12, are stored. Subsequently, the count results of the first and second X-ray detectors 31a and 31b are acquired, and the first and second count data indicative of X-ray energy spectra are output. In addition, the tube voltage or tube current at the time of X-ray irradiation is estimated based on the comparison of energy spectra between the second count data and each of the plural reference count data. Further, using the energy spectrum calculated based on the estimated tube voltage or tube current, the first count data obtained together with the second count data is corrected. Moreover, based on the corrected first count data, the medical image data is reconstructed. Thereby, the variation of the energy spectrum of X-rays radiated from the X-ray tube 12 can be corrected, and the tomogram at each energy or each energy band can exactly be reconstructed.

Additionally, in step ST3, when the tube voltage of the reference count data with the highest similarity degree, among the calculated similarity degrees, is estimated as the tube voltage at the time of irradiation to the human body P, the tube voltage can easily and quickly be estimated.

Additionally, in step ST3, when the relationship between the calculated similarity degrees and the tube voltages of the reference count data having these similarity degrees is approximated by a curve, and the tube voltage relating to the similarity degree at the time when the curve takes the maximum value is estimated as the tube voltage at the time of irradiation to the subject P, the tube voltage can be estimated with high precision.

Additionally, in step ST4, based on the estimated tube voltage and two reference count data corresponding individually to two tube voltages between which the estimated tube voltage lies, the two energy spectra indicated by these reference count data are interpolated, and thereby the energy spectrum of X-rays radiated with the estimated tube voltage is estimated. In this case, the energy spectrum corresponding to the estimated tube voltage can be estimated with high precision.

Additionally, in step ST5, the correction processor 62 may correct the tube voltage at the time of irradiation, instead of correcting the first count data. As described above, such a case is conceivable that, despite the tube voltage to be irradiated being 100.0 kV, the tube voltage that is estimated (that is thought to have been actually irradiated) varies and lowers to a low value such as 99.8 kV. In this case, the correction processor 62 increases the voltage of the tube voltage for irradiation. Specifically, while the value of the tube voltage is being gradually increased, the estimation process of the tube voltage is continued, and imaging is executed by adopting the tube voltage at the time point when the estimated tube voltage has reached 100.0 kV. When the estimated tube voltage is higher than the tube voltage to be irradiated, the tube voltage is adjusted while, conversely, the voltage of the tube voltage is being gradually lowered.

Second Embodiment

An X-ray CT apparatus according to a second embodiment is described with reference to FIG. 1.

The second embodiment is a modification of the first embodiment, and uses a kV switching method of switching, on a view-by-view basis, the tube voltage between a high voltage (e.g., 135 kV) and a low voltage (e.g., 80 kV) during imaging.

In accordance with this, as the X-ray tube 12, use is made of an X-ray tube which is driven while the tube voltage is being temporally modulated.

In addition, the correction processor 62 includes a function of estimating the temporally modulated tube voltage, based on the comparison of energy spectra between the second count data and each of a plurality of reference count data.

Figure 5:
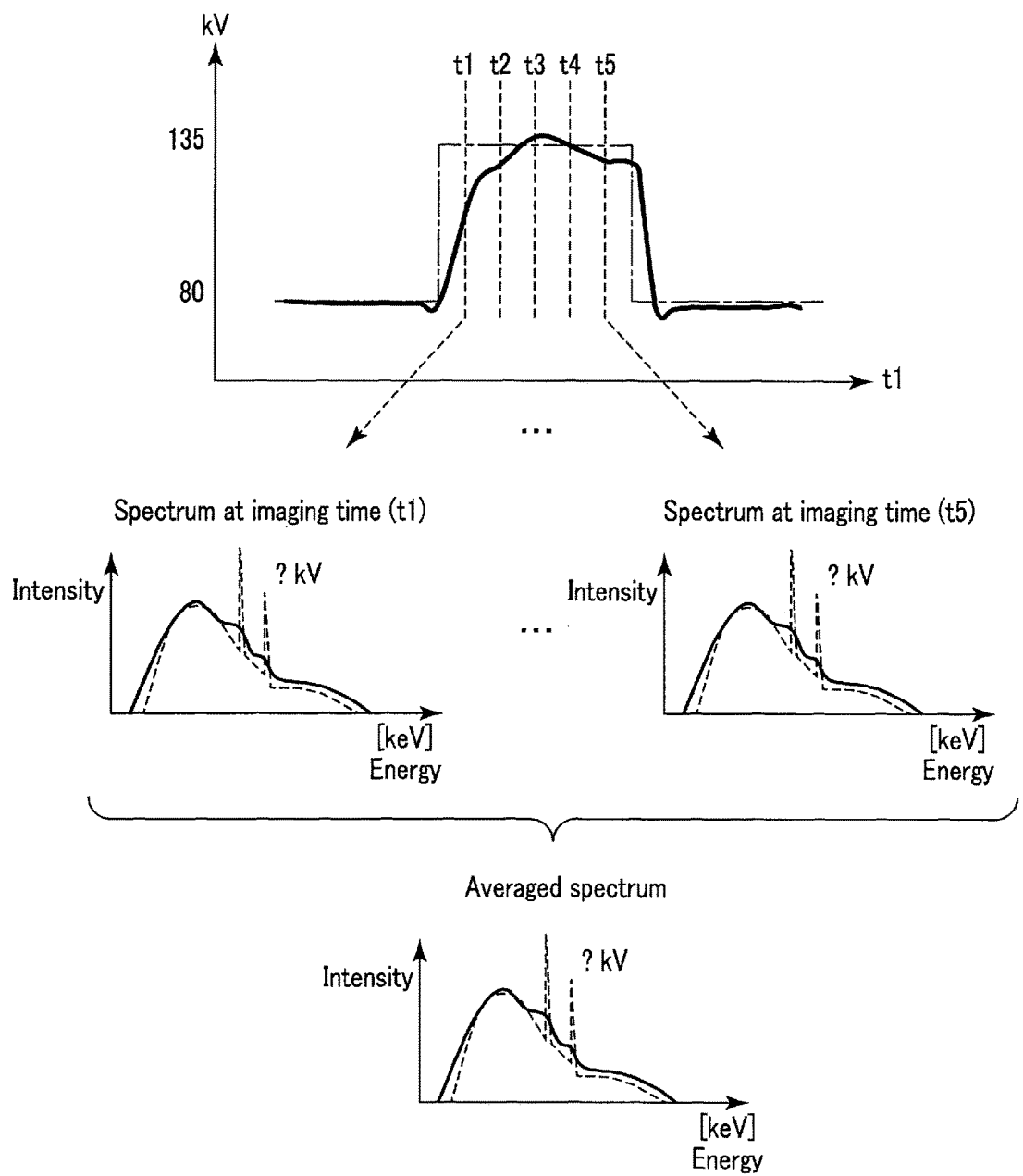
FIG. 5 is a diagram for explaining second count data in a second embodiment.

Here, as illustrated in FIG. 5 by way of example, as the second count data that is the object of comparison, use is made of a result obtained by averaging a plurality of second count data acquired at a plurality of time points (e.g., t1~t5) in one view in which the target value of the tube voltage is identical (e.g., 135 kV). Specifically, the second count data that is the object of comparison has an energy spectrum of X-rays, as illustrated in a lower part of FIG. 5. In an upper part of FIG. 5, the ordinate indicates a tube voltage, and the abscissa indicates time points. In addition, in the upper part of FIG. 5, a rectangular wave of a one-dot-and-dash line indicates "target value of tube voltage", and an obtuse rectangular wave of a solid line indicates an actually measured value of the tube voltage. In the meantime, when the tube voltage is not switched during imaging (when the actually measured value of the tube voltage is constant), a result obtained by averaging plural second count data acquired at plural arbitrary time points may be set to be the second count data that is the object of comparison. In this case, the average value of the temporally modulated tube voltage is obtained as an estimation result.

The remaining configuration is the same as in the first embodiment.

Next, the operation of the X-ray CT apparatus with the above-described configuration is described with reference to the flowchart of FIG. 4.

It is now assumed that step ST1 was executed as described above.

After step ST1, in the X-ray CT apparatus, the X-ray tube 12 is driven while the tube voltage is being temporally modulated, and the subject P is imaged.

The data-acquisition module (DAS) 32 acquires count results of the first and second X-ray detectors 31a, 31b, and outputs first and second count data indicative of X-ray energy spectra to the correction processor 62.

Upon receiving the first and second count data, the correction processor 62 obtains the second count data that is the object of comparison, by averaging plural second count data acquired at plural time points in one view in which the target value of the tube voltage is identical.

Thereafter, the correction processor 62 estimates the temporally modulated tube voltage, based on the comparison of energy spectra between the second count data that is the object of comparison and each of the plural reference count data. Specifically, in the same manner as described above, steps ST2 and ST3 are executed by using the second count data that is the object of comparison.

Subsequently, in the same manner as described above, the X-ray CT apparatus executes steps ST4 and ST5, and reconstructs the medical image data of the subject P. However, the arithmetic operation for the reconstruction is changed, as needed, in accordance with the kV switching method.

As has been described above, according to the present embodiment, even when the tube voltage is temporally modulated and the X-ray tube 12 is driven, the temporally modulated tube voltage is estimated based on the comparison of energy spectra between the second count data and each of the plural reference count data. Thereby, even in the case where the kV switching method is used, the same advantageous effects as in the first embodiment can be obtained.

Incidentally, in the present embodiment, the second count data at plural time points are averaged, and the tube voltage is estimated based on the obtained second count data. However, this embodiment may be modified such that tube voltages at plural time points are estimated based on the second count data at plural time points, and the tube voltage is estimated by averaging the obtained results.

Third Embodiment

Next, an X-ray CT apparatus according to a third embodiment is described with reference to FIG. 1.

The third embodiment is a modification of the first or second embodiment. For example, based on the body type, etc. of the subject P, the regions of the first and second X-ray detectors 31*a*, 31*b* are made changeable.

As a supplementary description, the first and second X-ray detectors 31*a*, 31*b* are used by dividing the X-ray detector 31 into two regions. However, it is possible that this division is improper, depending on the body type, etc. of the subject P. For example, depending on the body type, etc. of the subject P, it is possible that a part of the subject P covers the second region corresponding to the second X-ray detector 31*b*.

Accordingly, in this embodiment, the regions of the first and second X-ray detectors 31*a*, 31*b* are made changeable. For example, the region of the second X-ray detector 31*b* may be changed from the left-side end region of the X-ray detector 31 to the right-side end region. Alternatively, while the left-side end region of the X-ray detector 31 is used as the region of the second X-ray detector 31*b*, the number of columns of this end region may be changed.

Accordingly, the input module (input interface circuitry) 66 accepts, in accordance with an operation by the operator, an input signal for switching the regions that are used as the first and second X-ray detectors 31*a*, 31*b*. In addition, the input module 66 sends the accepted input signal to the data-acquisition module (DAS) 32 via the system controller 61 and gantry control transmission module 41.

The data-acquisition module (DAS) 32 includes a control function (controller) which switches, based on the input signal that the input module 66 accepted, the regions of the X-ray detector 31, which are used as the first and second X-ray detectors 31*a*, 31*b*.

According to the above-described configuration, the input module 66 accepts the input signal in advance. Based on the input signal that the input module 66 accepted, the data-acquisition module (DAS) 32 switches the regions of the X-ray detector 31, which are used as the first and second X-ray detectors 31*a*, 31*b*.

In the present embodiment, after the regions, which are used as the first and second X-ray detectors 31*a*, 31*b*, were switched in advance, the same operation as in the first or second embodiment is performed. Thus, the same advantageous effects as in the first or second embodiment can be obtained.

Fourth Embodiment

Next, an X-ray CT apparatus according to a fourth embodiment is described with reference to FIG. 1.

The fourth embodiment is a modification of any one of the first to third embodiments, and the similarity degree is calculated from partial regions of energy spectra.

Accordingly, the correction processor 62 divides the second count data and each of the plural reference count data into a plurality of energy bands, and calculates the similarity degree by comparing the second count data and reference count data of at least one energy band of the respective energy bands.

For example, it is assumed that each of the second count data (solid line) and the plural reference count data (broken line) are divided into four energy bands B1 to B4. This division may be made by the operator setting thresholds of energy bands. In addition, this division is merely an example, and the division may be changed to other division, as needed.

Here, the first energy band B1 is a band on the lowest energy side, in which the inclination is large. Incidentally, the magnitude of the inclination is a magnitude in a case of a comparison with inclinations of the other energy bands.

The second energy band B2 neighbors the first energy band B1. The second energy band B2 is a band on a higher energy side than the band B1, in which the inclination is small.

The third energy band B3 neighbors the second energy band B2. The third energy band B3 is a band on a higher energy side than the band B2, in which the inclination varies largely.

The fourth energy band B4 neighbors the third energy band B3. The fourth energy band B4 is a band on a higher energy side than the band B3, in which the inclination is small.

Figure 6:
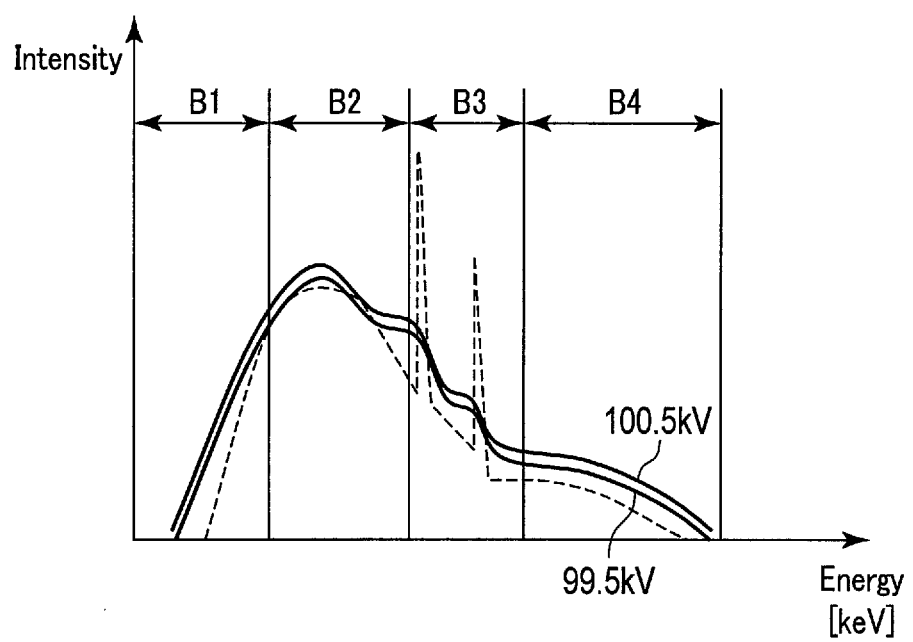
FIG. 6 is a diagram for explaining a plurality of energy bands in a fourth embodiment.

These four energy bands B1 to B4 vary in an up-and-down direction in accordance with the tube voltage. Here, as illustrated in FIG. 6, since the inclinations in the second and fourth energy bands B2 and B4 are small, curves do not overlap before and after a variation corresponding to the tube voltage (99.5 kV~100.5 kV), and a difference tends to easily occur.

Thus, the correction processor 62 calculates the similarity degree by comparing the data of at least one energy band B2 or B4 of the divided energy bands B1 to B4.

The other configuration is the same as in any one of the first to third embodiments.

Next, the operation of the X-ray CT apparatus with the above-described configuration is described with reference to FIG. 4.

It is now assumed that step ST1 was executed as described above.

After step ST1, in the X-ray CT apparatus, the X-ray tube 12 is driven, and the subject P is imaged.

The data-acquisition module (DAS) 32 acquires count results of the first and second X-ray detectors 31*a*, 31*b*, and outputs first and second count data indicative of X-ray energy spectra to the correction processor 62.

Upon receiving the first and second count data, the correction processor 62 divides the second count data and each of the plural reference count data into a plurality of energy bands, and compares the second count data and reference count data of at least one energy band of the respective divided energy bands, thereby calculating the similarity degree (ST2).

Subsequently, in the same manner as described above, the X-ray CT apparatus executes steps ST3 to ST5, and reconstructs the medical image data of the subject P.

As has been described above, according to the present embodiment, the second count data and each of the plural reference count data are divided into the plural energy bands B1 to B4. In addition, the similarity degree is calculated by comparing the data of at least one energy band B2 or B4 of the respective energy bands B1 to B4.

Thereby, in the present embodiment, in addition to the same advantageous effects as in the first to third embodiments, the load of arithmetic operations for calculating the similarity degree can be decreased, compared to the case of a comparison over all energy bands.

According to at least one of the above-described embodiments, the tube voltage or tube current at the time of X-ray irradiation is estimated based on the comparison of energy spectra between the second count data and each of the plural reference count data. In addition, the first count data obtained together with the second count data is corrected by using an energy spectrum calculated based on the estimated tube voltage or tube current. Furthermore, the medical image data is reconstructed based on the corrected first count data. Thereby, the variation of the energy spectrum of X-rays radiated from the X-ray tube 12 can be corrected, and the tomogram at each energy or each energy band can exactly be reconstructed.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. An X-ray computed tomography apparatus, comprising:
   an X-ray tube configured to radiate X-rays;
   a first X-ray detector configured to count X-ray photons in a first region of the radiated X-rays, and to acquire energy of the X-ray photons;
   a second X-ray detector configured to count X-ray photons in a second region of the radiated X-rays, and to acquire energy of the X-ray photons;
   count result acquisition circuitry configured to acquire count results of the first X-ray detector and the second X-ray detector, and to output first count data and second count data indicative of energy spectra of the X-rays;
   memory circuitry storing a plurality of reference count data indicative of energy spectra of X-rays, which are associated with a plurality of tube voltages or a plurality of tube currents for radiating the X-rays from the X-ray tube;
   estimation circuitry configured to estimate a tube voltage or a tube current at a time of X-ray irradiation, based on a comparison of energy spectra between the second count data and each of the plurality of reference count data;
   correction circuitry configured to correct the first count data acquired together with the second count data, by using an energy spectrum calculated based on the estimated tube voltage or tube current; and
   reconstruction circuitry configured to reconstruct medical image data, based on the corrected first count data.

2. The X-ray computed tomography apparatus of claim 1, wherein the estimation circuitry is further configured to calculate a plurality of similarity degrees by comparing the second count data and each of the plurality of reference count data, and estimate a tube voltage or a tube current corresponding to reference count data having a highest similarity degree of the calculated plurality of similarity degrees, as the tube voltage or the tube current at the time of X-ray irradiation.

3. The X-ray computed tomography apparatus of claim 2, wherein the estimation circuitry is further configured to calculate the energy spectrum of the radiated X-rays, by interpolating the estimated tube voltage or tube current and two of said plurality of reference count data corresponding individually to two tube voltages of the plurality of tube voltages or two tube currents of the plurality of tube currents between which the estimated tube voltage or tube current lies.

4. The X-ray computed tomography apparatus of claim 2, wherein the estimation circuitry is further configured to divide the second count data and each of the plurality of reference count data into a plurality of energy bands, and calculate the plurality of similarity degrees by comparing the second count data and the plurality of reference count data of at least one energy band of the respective energy bands.

5. The X-ray computed tomography apparatus of claim 1, wherein the estimation circuitry is further configured to calculate a plurality of similarity degrees between the second count data and the plurality of reference count data, approximate a curve using the plurality of similarity degrees, and estimate a tube voltage or a tube current based on a maximum value of the curve, as the tube voltage or the tube current at the time of the X-ray irradiation.

6. The X-ray computed tomography apparatus of claim 1, wherein the memory circuitry stores the plurality of reference count data indicative of the X-ray energy spectra, which were obtained from the second X-ray detector and the count result acquisition circuitry, by radiating X-rays from the X-ray tube with a plurality of preset tube voltages or a plurality of preset tube currents.

7. The X-ray computed tomography apparatus of claim 1, further comprising a table on which a subject is placed,
   wherein the first region includes at least a region corresponding to the subject placed on the table, and
   the second region is a region different from the first region.

8. The X-ray computed tomography apparatus of claim 1, wherein the second X-ray detector is provided continuous with an end portion of the first X-ray detector.

9. The X-ray computed tomography apparatus of claim 1, wherein the first X-ray detector and the second X-ray detector are two regions of an X-ray detector, and
   the X-ray computed tomography apparatus further comprises:
      input interface circuitry configured to accept an input signal; and
      a controller configured to switch the two regions of the X-ray detector, which are used as the first X-ray detector and the second X-ray detector, based on the input signal.

10. The X-ray computed tomography apparatus of claim 1, wherein the X-ray tube is driven while the tube voltage is being temporally modulated, and
   the estimation circuitry is further configured to estimate the temporally modulated tube voltage, based on a comparison of energy spectra between the second count data and each of the plurality of reference count data.

* * * * *